United States Patent
Hong et al.

(10) Patent No.: US 10,905,896 B2
(45) Date of Patent: Feb. 2, 2021

(54) TREATMENT DEVICE FOR SCALP

(71) Applicant: LG ELECTRONICS INC., Seoul (KR)

(72) Inventors: Sungho Hong, Seoul (KR); Munseong Kang, Seoul (KR); Sangwon Kim, Seoul (KR); Heejung Kim, Seoul (KR); Heejin Park, Seoul (KR); Yongju Yang, Seoul (KR); Gueisam Lim, Seoul (KR); Dongwon Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 200 days.

(21) Appl. No.: 15/866,653

(22) Filed: Jan. 10, 2018

(65) Prior Publication Data
US 2019/0126061 A1  May 2, 2019

(30) Foreign Application Priority Data

Oct. 31, 2017 (KR) .......................... 10-2017-0143301

(51) Int. Cl.
*A61N 5/06* (2006.01)
*A61N 5/067* (2006.01)

(52) U.S. Cl.
CPC ...... *A61N 5/0617* (2013.01); *A61H 2205/021* (2013.01); *A61N 2005/067* (2013.01); *A61N 2005/0643* (2013.01); *A61N 2005/0659* (2013.01); *A61N 2005/0661* (2013.01)

(58) Field of Classification Search
CPC ...................... A61N 5/0617; A61N 2005/0643
See application file for complete search history.

(56) References Cited

U.S. PATENT DOCUMENTS

| | | | |
|---|---|---|---|
| 2002/0128696 A1* | 9/2002 | Pearl | A61N 5/0617 607/89 |
| 2005/0166863 A1* | 8/2005 | Park, III | A01K 13/002 119/625 |
| 2005/0251242 A1* | 11/2005 | Bousfield | A61N 5/0617 607/150 |
| 2008/0125835 A1* | 5/2008 | Laurent | A61N 5/0617 607/89 |
| 2008/0172112 A1* | 7/2008 | Gourgouliatos | A61N 5/0617 607/89 |

(Continued)

FOREIGN PATENT DOCUMENTS

| | | |
|---|---|---|
| JP | 2010-131260 A | 6/2010 |
| KR | 10-2004-0012937 A | 2/2004 |

(Continued)

*Primary Examiner* — Gary Jackson
*Assistant Examiner* — Zahed Kabir
(74) *Attorney, Agent, or Firm* — Birch, Stewart, Kolasch & Birch, LLP

(57) ABSTRACT

A treatment device for a scalp including a body that defines an exterior design and has one surface in which a plurality of light irradiation holes are formed, a light generation unit provided in the body and a beam splitter that dividedly refractionates light generated in the light generation unit into a plurality of lights and guides the lights toward the plurality of the light irradiation holes and a travel direction of the light generated in the light generation unit is different from a travel direction of the light passing the beam splitter.

13 Claims, 7 Drawing Sheets

(56) References Cited

U.S. PATENT DOCUMENTS

2009/0270845 A1* 10/2009 Birmingham ........ A61N 5/0617
  606/2
2010/0004570 A1* 1/2010 Torres Martin .... A61H 23/0254
  601/17
2011/0152979 A1* 6/2011 Driscoll ............... A61N 5/0616
  607/93

FOREIGN PATENT DOCUMENTS

| KR | 10-2005-0086650 A | 8/2005 |
| KR | 20-2009-0003968 A | 4/2009 |
| KR | 10-1009462 B1 | 1/2011 |
| KR | 10-1045214 B1 | 6/2011 |
| KR | 10-1076057 B1 | 10/2011 |
| KR | 10-2012-0021417 A | 3/2012 |
| KR | 10-2015-0130742 A | 11/2015 |
| WO | WO 02/102228 A2 | 12/2002 |

* cited by examiner

TREATMENT DEVICE FOR SCALP

CROSS-REFERENCE TO RELATED APPLICATIONS

This application claims priority to Korean Patent Application No. 10-2017-0143301 filed on Oct. 31, 2017 in Korea, the entire contents of which is hereby incorporated by reference in its entirety.

BACKGROUND OF THE DISCLOSURE

Field of the Disclosure

Embodiments of the present disclosure relate to a treatment device for a scalp, more specifically, a treatment device for a scalp which is capable of extensively radiating light to a human scalp, using the minimum of light sources and automatically controlling the light generated from a light source.

Background of the Disclosure

Recently, many people have the loss of hair which is caused by acquired environment factors, especially, stress and such environment factors. When the loss of hear is developed by the various factors which weakens a state of the scalp, people could have side effects such as difficulty in social life and then mental distress because of the hair loss To prevent such the loss of hair, many types of scalp massage devices for stimulating the scalp have been used a lot. Such a scalp massage device is configured to stimulate hair roots, usually using a diaphragm which is vibrated by a motor. However, the scalp stimulation using the vibration has the limited strength of the stimulation. In other words, if heightening the applied vibration to enhance the stimulation applied to the scalp, the brain might be given a jolt or shock. Accordingly, the stimulation applied by the vibration is limited not to give the brain the jolt or shock and the scalp could fail to be stimulated enough to deteriorate the effect of hair loss prevention disadvantageously.

In addition, a scalp care device or a scalp treatment device which radiates light to the scalp is disclosed. As one of examples, Korean Patent No. 10-1506819 discloses 'Apparatus for massaging scalp and skin' which uses light irradiation.

A conventional apparatus for massaging scalp and skin by using light irradiation has a disadvantage that light is radiated on some region (or a narrow area) by using one light source.

The distance between the scalp and a light irradiation hole has to be controlled to be an optimal distance so as to minimize the stimulation of the scalp or maximize the massage effect.

Furthermore, the conventional apparatus for massaging the scalp has another disadvantage that a user has to adjust the distance between the light irradiation hole and the scalp randomly.

Still further, when it covers the scalp, the user's hair might interfere with the light radiated to reach the scalp disadvantageously.

SUMMARY OF THE DISCLOSURE

Accordingly, an object of the present invention is to address the above-noted and other problems. Embodiments of the present disclosure may provide a treatment device for a scalp which is capable of radiating light to the scalp in a wide range by using the least number of light sources.

Embodiments of the present disclosure may also provide a treatment device for a scalp which may control light to be automatically radiated when a distance between a light irradiation hole and the scalp is in a preset range.

Embodiments of the present disclosure may also provide a treatment device for a scalp which may prevent a user's hair from interfering with the light irradiation on the scalp.

Embodiments of the present disclosure may also provide a treatment device for a scalp comprising a body which defines an exterior design and having one surface in which a plurality of light irradiation holes are formed; a light generation unit provided in the body; and a beam splitter configured to dividedly refractionate the light generated in the light generation unit into a plurality of lights and guide the lights toward the plurality of the light irradiation holes, wherein a travel direction of the light generated in the light generation unit is different from a travel direction of the light having passed the beam splitter.

The beam splitter may refractionate the travel path of the light into a plurality of travel paths by reflecting the light generated in the light generation unit.

The refractionated lights may be guided to the different light irradiation holes, respectively.

The treatment device for the scalp may further comprise a controller configured to control the light generation unit; and a distance sensor provided in one surface of the body and controllable by the controller, wherein when a distance between the surface of the body and the scalp is within a preset range of distances, light is automatically generated in the light generation unit.

The treatment device for the scalp may further comprise a plurality of combteeth projected from the surface of the body, wherein the preset range of the distances is determined based on the length of the combteeth.

The preset range of the distances may be determined by applying a preset tolerance to the length of the combteeth.

The beam splitter may comprise a reflection unit comprising a plurality of reflective surfaces configured to reflect the light generated in the light generation unit; a first lens spaced a preset distance apart from the reflection unit and configured to widen an irradiation range of the lights reflected by the reflection unit; and a plurality of guide units configured to guide the lights having passed the first lens to the plurality of the light irradiation holes, respectively.

The first lens may comprise a plurality of convex portions which are convex toward the plurality of the reflective surfaces.

The plurality of the reflective surfaces may be provided in a lower surface of the reflection unit, and the lower surface of the reflection unit may be stepped in a direction which gets closer toward the first lens as getting farther from the light generation unit.

The beam splitter may comprise a reflection unit comprising a plurality of reflective surfaces configured to reflect the light generated in the light generation unit; and a plurality of guide units configured to guide the lights having passed the first lens to the plurality of the light irradiation holes, respectively, and the reflection unit and the guide units are integrally formed with each other.

A second lens configured to widen an irradiation range of the lights guided by the guide units may be provided in an end of each guide unit.

The plurality of the reflective surfaces may be provided in an upper surface of the reflection unit, and the upper surface of the reflection unit may be stepped in a direction which gets closer to the first lens as getting farther from the light generation unit.

The beam splitter may be formed of a bundle of glass fibers extended toward the light irradiation holes, and each of the glass fibers may be bent toward each corresponding one of the light irradiation holes.

The light generation unit may comprise a light source; a third lens arranged between the light source and the beam splitter and configured to facilitate the horizontal irradiation of the light toward the beam splitter.

The treatment device for the scalp may further comprise a wind generation unit provided in the body, wherein the wind generated in the wind generation unit is exhausted via one or more outlet holes formed in the surface of the body.

A plurality of outlet holes may be arranged at preset intervals, and one or more of the light irradiation holes may be arranged between each two neighboring outlet holes.

The treatment device for the scalp may further comprise a guide path configured to guide the wind generated in the wind generation unit toward the plurality of the outlet holes.

The treatment device for the scalp may further comprise a controller configured to control the light generation unit and the wind generation unit; and a distance sensor provided in the surface of the body and controllable by the controller, wherein when a distance between the surface of the body and the scalp is within a preset range of distances, the wind generated in the wind generation unit is automatically generated.

The combteeth may be extended as long as within the preset range of the distances.

According to at least one of the embodiments, light may be irradiated in the wide range of the scalp, using the minimum number of the light sources.

Furthermore, when the distance between the light irradiation holes and the scalp is within the present range of the distances, light may be automatically irradiated.

Still further, the treatment device for the scalp is capable of preventing the interference of the user's hair with the light irradiation.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

DESCRIPTION OF SPECIFIC EMBODIMENTS

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be directly connected with the other element or intervening elements may also be present. In contrast, when an element is referred to as being "directly connected with" another element, there are no intervening elements present.

The terminology used in the present disclosure is used only to describe specific embodiments, not intended to limit the present disclosure. A singular representation may include a plural representation unless it represents a definitely different meaning from the context.

Terms such as "include" or "has" are used herein and should be understood that they are intended to indicate an existence of several components, functions or steps, disclosed in the specification, and it is also understood that greater or fewer components, functions, or steps may likewise be utilized.

Figure 1:
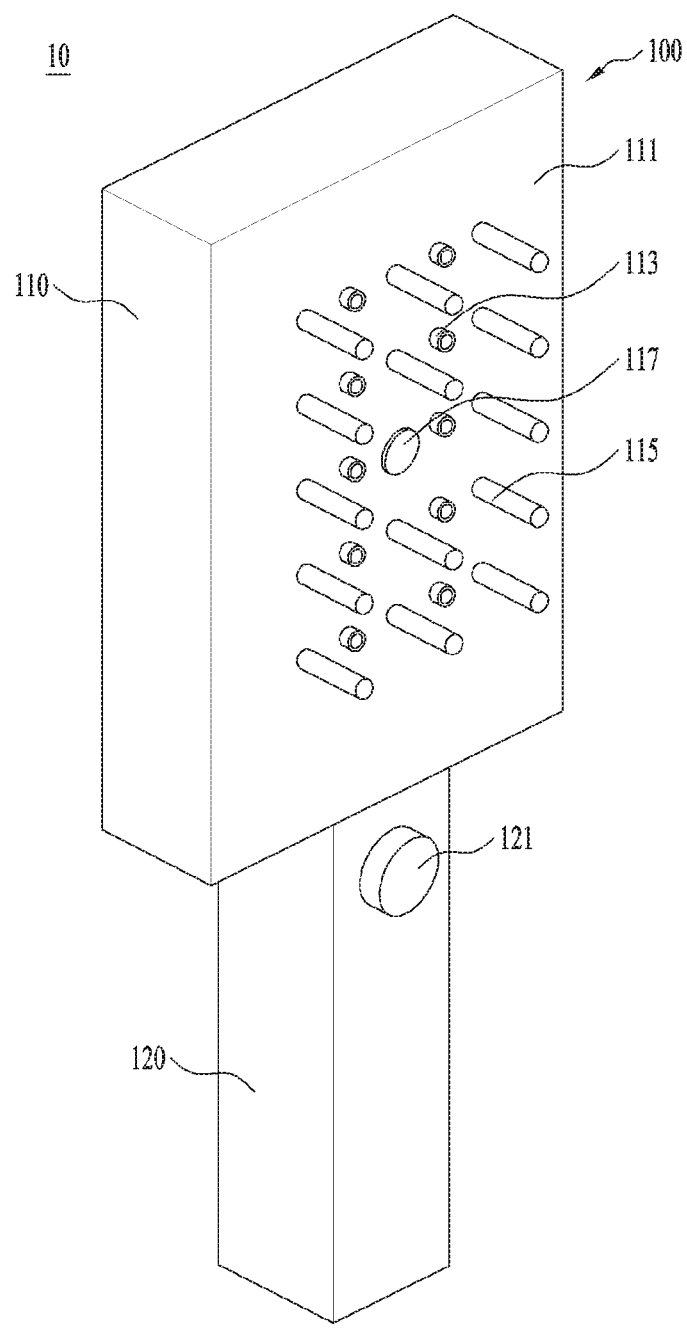
FIG. 1 is a perspective diagram illustrating a treatment device for a scalp in accordance with a first embodiment of the present disclosure.
Figure 2:
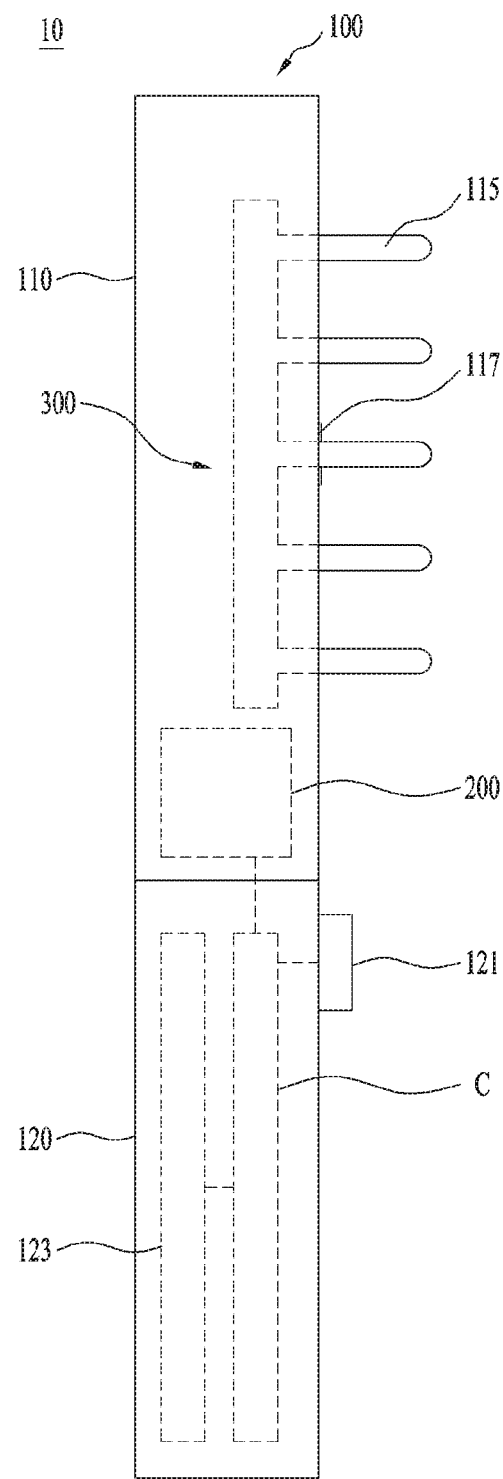
FIG. 2 is a side view of the treatment device for the scalp shown in FIG. 1.

FIG. 1 is a perspective diagram illustrating a treatment device for a scalp in accordance with a first embodiment of the present disclosure. FIG. 2 is a side view of the treatment device for the scalp shown in FIG. 1.

Referring to FIGS. 1 and 2, the treatment device for the scalp in accordance with the first embodiment may include a body 100, a light generation unit 200 provided in the body 100, and a beam splitter 300 configured to split the light generated in the light generation unit 200 into a plurality of lights.

The body may define an exterior design of the treatment device for the scalp 100 and a plurality of light irradiation holes 113 may be formed in one surface 111 of the body 100. The light generated in the light generation unit 200 may be irradiated outside the treatment device for the scalp 10 via the light irradiation holes 113. At this time, the surface 111 of the body 100 may be the surface located toward the user's scalp.

The light generation unit 100 may be configured to generate light. In other words, the light generation unit 200 may be formed to generate (or irradiate) lasers, infrared rays or ultraviolet rays. As one example, the light generation unit 200 may include LED as a light source.

The beam splitter 300 may be configured to split the light generated in the light generation unit 200 into a plurality of beams and guide them toward the light irradiation holes 113. In other words, the light generated in the light generation unit 200 is fractionatedly irradiated to the light irradiation holes 113 by the beam splitter 300. For example, the beams or lights fractionated by the beam splitter 300 may be guided to different light irradiation holes 113, respectively.

Each of the light irradiation holes 113 may not require one light generation unit 200, so that the structure and control can become simple and the lights may be irradiated to a wide range via the plurality of the light irradiation holes 113. In the illustrated embodiment, the light irradiation holes 113 are arranged along a longitudinal direction of the body 100 in two lines and one light generation unit may be arranged in each one line.

The beam splitter 300 is configured to change a travel path of the light generated in the light generation unit 200. In other words, the travel direction of the light generated in the light generation unit 200 may be different from that of the light having passed the beam splitter 300. For example, the light generated in the light generation unit 200 may travel along the longitudinal direction of the body 100 and the travel path may be changed toward one surface (a front surface) of the body 100 while passing the beam splitter 300.

That is realized because the beam splitter 300 uses the reflection of the lights on a plurality of reflective surfaces or the guide of the lights via a bundle of glass fibers while the travel path of the light generated in one light generation unit 200 is fractionated into a plurality of travel paths.

The treatment device for the scalp 10 may further include a controller (C) implemented to control the light generation unit 200 and a distance sensor 117.

The controller (C) is formed as a printed circuit board for switching on and off the light generation unit 200. More specifically, the controller (C) is capable of selectively switching on and off the light generation unit 200 based on a signal received from the distance sensor 117.

The distance sensor 117 may be provided in the surface (or the front surface) of the body 100. In other words, the distance sensor 117 may be configured to sense a distance with the user's scalp. For example, the distance sensor 117 may be arranged on the same plane with the surface 111 of the body 100, so that it can sense the distance between the surface 111 of the body 100 and the user's scalp.

More specifically, when the distance between the surface 111 of the body 100 and the scalp sensed by the distance sensor 117 is within a preset range of distances, light may be automatically generated in the light veneration unit 200. Of course, the light is generated in the light generation unit 200 on condition that a power signal is input by a power button which will be described later.

The controller (C) is implemented to control the light generation unit 200 to generate the light when the distance between the surface 111 of the body 100 and the scalp sensed by the distance sensor 117 is in the preset range.

At this time, the preset range of the distances may be determined through experiments as a range in which the care of the scalp can be optimized while the user's scalp is not damaged by the light.

The treatment device for the scalp 10 may further include a plurality of combteeth 115 projected from the surface 111 of the body 100. The combteeth 115 may be coupled to or integrally formed with the body 100.

At this time, the preset range of the distances mentioned above may be determined based on the length of the combteeth 115. In other words, the combteeth 115 may be extended less long as within the range of the distances. Accordingly, when the user locates the combteeth 115 in contact with an area of the scalp which needs treatment or care, light may be generated in the light generation unit 200 by the control of the controller (C).

The user need not adjust an optimal distance with the scalp randomly. Only when the user locating the combteeth 115 to contact with the scalp, the distance between the light irradiation holes 113 and the scalp may be kept as the optimal distance.

A tolerance is applied to the length of the combteeth 115 to set the preset range of the distances. For example, a range of distances from a preset plus tolerance to a preset minus tolerance based on the length of the combteeth 115 may be set as the preset range of the distances.

The treatment device for the scalp 10 may further include a battery 123 for supplying electric power. More specifically, the body 100 may include a first body 110 for accommodating the light generation unit 200 and the beam splitter 300, and a second body 120 for accommodating the controller (C) and the battery 123.

The plurality of the light irradiation holes 113 and combteeth 115 may be provided in the first body 110. A power button 121 for inputting a power signal to the controller (C) may be provided in the second body 120.

The first body 110 and the second body 120 may be detachably coupled to each other. In this instance, the maintenance of the internal components provided in the body 100 may be easily performed. As an alternative example, the first body 110 and the second body 120 may be integrally formed with each other. In this instance, the durability of the body 100 may be enhanced.

According to the embodiment, the light irradiation for a wide scalp area may be enabled by using the minimum light generation units 200.

Moreover, the number of the light generation units 200 may be minimized so that the control logic of the light generation units 200 can become relatively simple and that the damage to the product caused by the heat generated in the light generation units 200 and the controller (C) can be minimized.

Hereinafter, referring to other drawings, embodiments of the beam splitter mentioned above will be described in detail.

Figure 3:
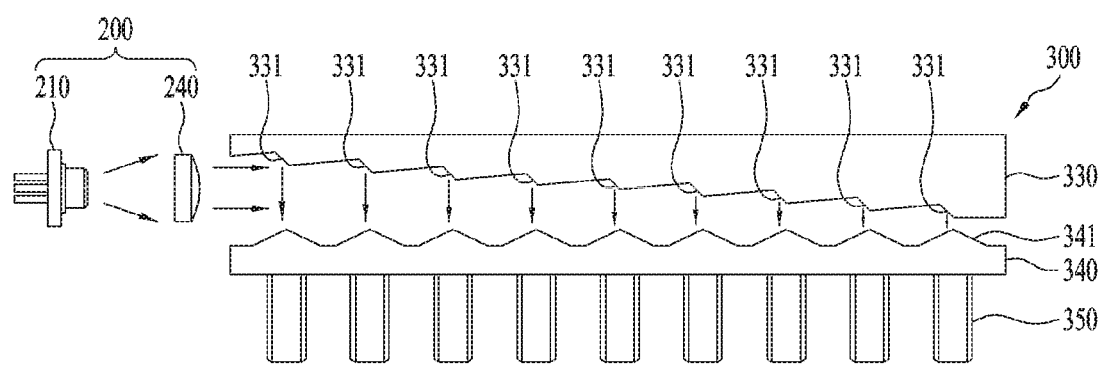
FIG. 3 is a diagram illustrating one embodiment of a beam splitter provided in the treatment device for the scalp.

FIG. 3 is a diagram illustrating one embodiment of a beam splitter provided in the treatment device for the scalp. An arrow shown in FIG. 3 illustrates a travel path of the light generated in the light generation unit.

Referring to FIG. 3, one embodiment of the beam splitter 300 may include a reflection unit 330 configured to refractionate light into a plurality of lights and reflect them, a first lens 340 for widen the irradiation range of the lights reflected by the reflection unit 330, and a plurality of guide units 350 for guide the light having passed the first lens 340 toward the plurality of the light irradiation holes 113.

The reflection unit 330 may include a plurality of reflective surfaces 331 for reflecting the light generated in the light generation unit 200. The reflective suffices 331 may be provided in a lower surface of the reflection unit 330. In other words, the reflective surfaces 331 may be realized by changing the shape of the lower surface of the reflection unit 330.

The reflection unit 330 may extend in a direction which gets farther from the light generation unit 200. The reflective surfaces 331 may be spaced a preset distance apart from each other along a longitudinal direction of the reflection unit 330.

More specifically, the reflective surfaces 331 may be inclined downwards in the direction which gets farther from the light generation unit 200. As getting farther from the light generation unit 200, the lower surface of the reflection unit 330 may be stepped in a direction which gets closer to the first lens 340. That is because the intensity of the light could become weaker as getting father from the light generation unit 200.

In other words, as the reflective surfaces 331 may be arranged closer to the first lens 340, as getting farther from the light generation unit 200. Accordingly, the intensity differences among the lights reflected on the reflective surfaces 331, respectively, may be minimized.

The first lens 340 may be arranged distant from the reflection unit 330. The light generated in the light generation unit 200 may be irradiated between the reflection unit 330 and the first lens 340 and along the longitudinal direction of the reflection unit 330. In other words, the light generated in the light generation unit 200 may be irradiated between the reflection unit 330 and the first lens 340 toward the plurality of the reflective surfaces 331.

The first lens 340 may include a convex or projected portion 341 toward the reflection unit 330. The convex portion 341 may be formed in a triangle shape which is convex toward the reflection unit 330.

More specifically, the first lens 340 may include a plurality of convex portions 341 corresponding to the plurality of the reflective surfaces 331. The irradiation angles of the lights reflected on the plurality of the reflective surfaces 331 may become larger while passing the corresponding convex portions 341, respectively. The irradiation range of the lights reflected on the reflective surfaces 331 may be widened by the first lens 340.

A plurality of guide units 350 may be provided, corresponding to the plurality of the convex portions 341. In other words, the plurality of the guide units 350 may correspond to the plurality of the reflective surfaces 331, respectively. The first lens 340 may be provided between the guide units 350 and the reflection units 330.

The guide units 350 may correspond to the light irradiation holes 131, respectively. Accordingly, the lights having passed the first lens 340 after reflected by the reflection unit 330 may be irradiated to the light irradiation holes 113 along the guide of the guide units 350.

The light generated in one light generation unit 200 may be uniformly irradiated to the plurality of the light irradiation holes 113 by the beam splitter 300.

Hereinafter, referring to another drawing, another embodiment of the beam splitter will be described.

Figure 4:
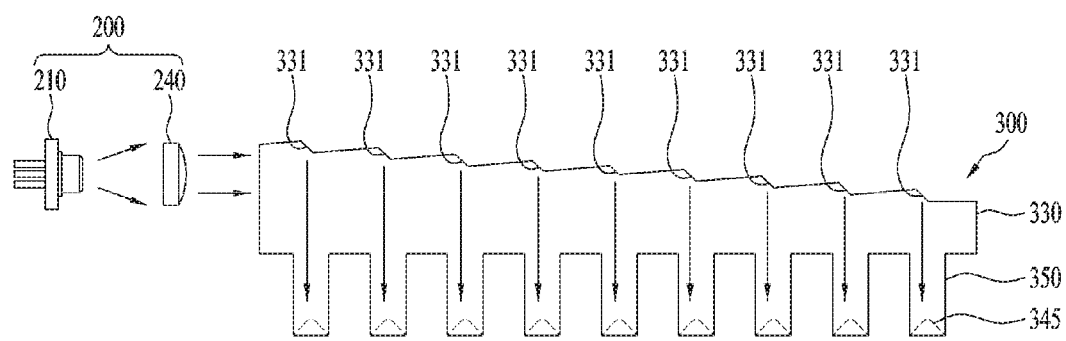
FIG. 4 is a diagram illustrating another embodiment of the beam splitter provided in the treatment device for the scalp.

FIG. 4 is a diagram illustrating another embodiment of the beam splitter provided in the treatment device for the scalp.

Referring to FIG. 4, the beam splitter 300 is arranged adjacent to the light generation unit 200 and it is equal to the embodiment of FIG. 3 that the beam splitter 300 is extended along a direction which gets farther from the light generation unit 200.

In the illustrated embodiment, the beam splitter 300 may include a reflection unit 330 having a plurality of reflective surfaces 331 configured to reflect the light generated in the light generation unit 200, and a plurality of guide units 350 configured to guide the light reflected on the plurality of the reflective surfaces 331 toward the plurality of the light irradiation holes 113.

A second lens 345 may be provided in an end of each guide unit 350 to widen the irradiation range of the lights guided by the guide units 350. In other words, the plurality of the second lenses 345 may be provided in ends of the corresponding guide units 350, respectively. The ends of the guide units 350 may mean the ends toward the light irradiation holes 113.

The reflection unit 330 may be integrally formed with the guide units 350. The reflective surfaces 331 may be formed in an upper surface of the reflection unit 330. In other words, the reflective surfaces 331 may be realized by changing the shape of the upper surface of the reflection unit 331.

The reflective surfaces 331 may be spaced a preset distance apart from each other along a longitudinal direction of the reflection unit 330.

More specifically, the plurality of the reflective surface surfaces 331 may be inclined in a direction which gets farther from the light generation unit 200. To allow the reflective surfaces 331 to gradually become closer to the first lens 340 as getting farther from the light generation unit 200, the plurality of the reflective surfaces 331 may be provided in the reflection unit 330. In other words, the upper surface of the reflection unit 330 may be stepped toward the second lenses 345 as getting farther from the light generation unit 200. That is because the intensity of the light could become weaker as getting farther from the light generation unit 200.

The reflective surfaces 331 may be arranged closer to the corresponding second lenses 345 as getting farther from the light generation unit 200, so as to minimize the intensity differences among the lights reflected on the reflective surfaces 331.

The light generated in the light generation unit 200 may be irradiated into the reflection unit 330. While passing through the reflection unit 330, the light may be reflected toward the guide units 350 by the reflective surfaces 331. In other words, the light generated in the light generation unit 200 may be irradiated into the reflection unit 330 and toward the reflective surfaces 331.

Each of the second lenses 345 may be formed in a convex shape toward the reflection unit 330. In other words, each of the second lenses 345 may be formed in a triangle shape which is convex toward the reflection unit 330.

The irradiation angle of the light reflected on the plurality of the reflective surfaces 331 may become larger while passing the second lenses 345. In other words, the irradiation range of the lights reflected on the reflective surfaces 331 may become wider by the second lenses 345.

The plurality of the guide units 350 may be provided, corresponding to the plurality of the reflective surfaces 331. The second lenses 345 may be provided in ends of the guide units 350, respectively.

The guide units 350 may correspond to the light irradiation holes 113, respectively. Accordingly, the light reflected by the reflection unit 330 may be guided to the plurality of the guide units 350 and irradiated to the corresponding light irradiation holes 113 after passing the second lenses 340.

As mentioned above, the light generated in one light generation unit 200 may be uniformly irradiated to the plurality of the light irradiation holes 113 by the beam splitter 300.

Hereinafter, referring to a further drawing, a further embodiment of the beam splitter will be described.

Figure 5:
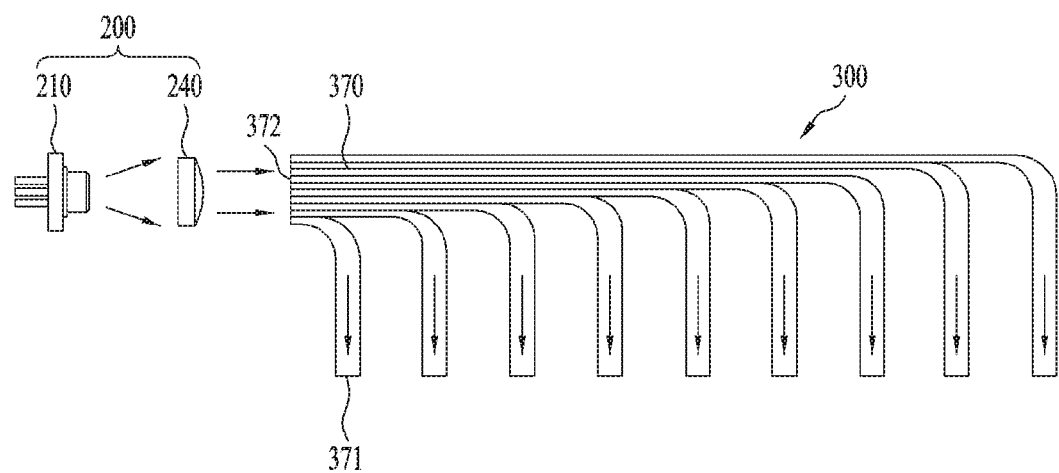
FIG. 5 is a diagram illustrating a further embodiment of the beam splitter provided in the treatment device for the scalp.

FIG. 5 is a diagram illustrating a further embodiment of the beam splitter provided in the treatment device for the scalp.

Referring to FIG. 5, the illustrated embodiment of the beam splitter 300 may be formed of a plurality of glass fibers 370. The bundle of the glass fibers 370 may be extended from the light generation unit 200 toward the light irradiation holes 113. The light generated in the light generation unit 200 may be guided toward the light irradiation holes 113 via the bundle of the glass fibers 370.

More specifically, each of the glass fibers may be bent toward each corresponding one of the light irradiation holes 113. In other words, each of the glass fibers may be bent toward each corresponding one of the light irradiation holes 113 arranged in different positions so that the bent point of each glass fiber may be different from the other ones.

The light generated in the light generation unit 200 may be dividedly refractionated into lights along a plurality of travel paths through the bundle of the glass fibers and guided to the corresponding light irradiation holes 113, respectively.

While the light is passing through the bundle of the glass fibers 370 (in other words, the light is passing through each of the glass fibers), full reflection is repeatedly generated and the irradiation range of the light at one end 371 of each glass fiber toward the light irradiation holes 113 may become widened.

Meanwhile, the light generation unit 200 shown in FIGS. 4 through 5 may include a light source 210 and a third lens 240.

The light source 210 may be an LED configured to generate and irradiate a laser light, an infrared light or an ultraviolet light. The third lens 240 may be disposed between the light source 210 and the beam splitter 300.

The third lens 240 may determine a travel path for horizontally irradiating the light generated by the light source toward the beam splitter 300. In other words, the third lens 240 may allow the light generated by the light source 210 to be irradiated in a longitudinal direction of the beam splitter 300.

In the embodiments shown in FIGS. 3 and 4, the light generated by the light source 210 may be intensively irradiated toward the plurality of the reflective surfaces 331 provided in the beam splitter 300 by the third lens 240.

Even in the embodiment shown in FIG. 5, the light generated by the light source 210 may be intensively irradiated toward the other end in opposite to one end of the glass fiber bundle 370. In this instance, the other end 372 may mean the end closer to the light source 210 than the light irradiation holes 113 in the longitudinal direction of the glass fiber bundle 370.

Next, referring to the other drawings, a treatment device for a scalp in accordance with the second embodiment will be described.

Figure 6:
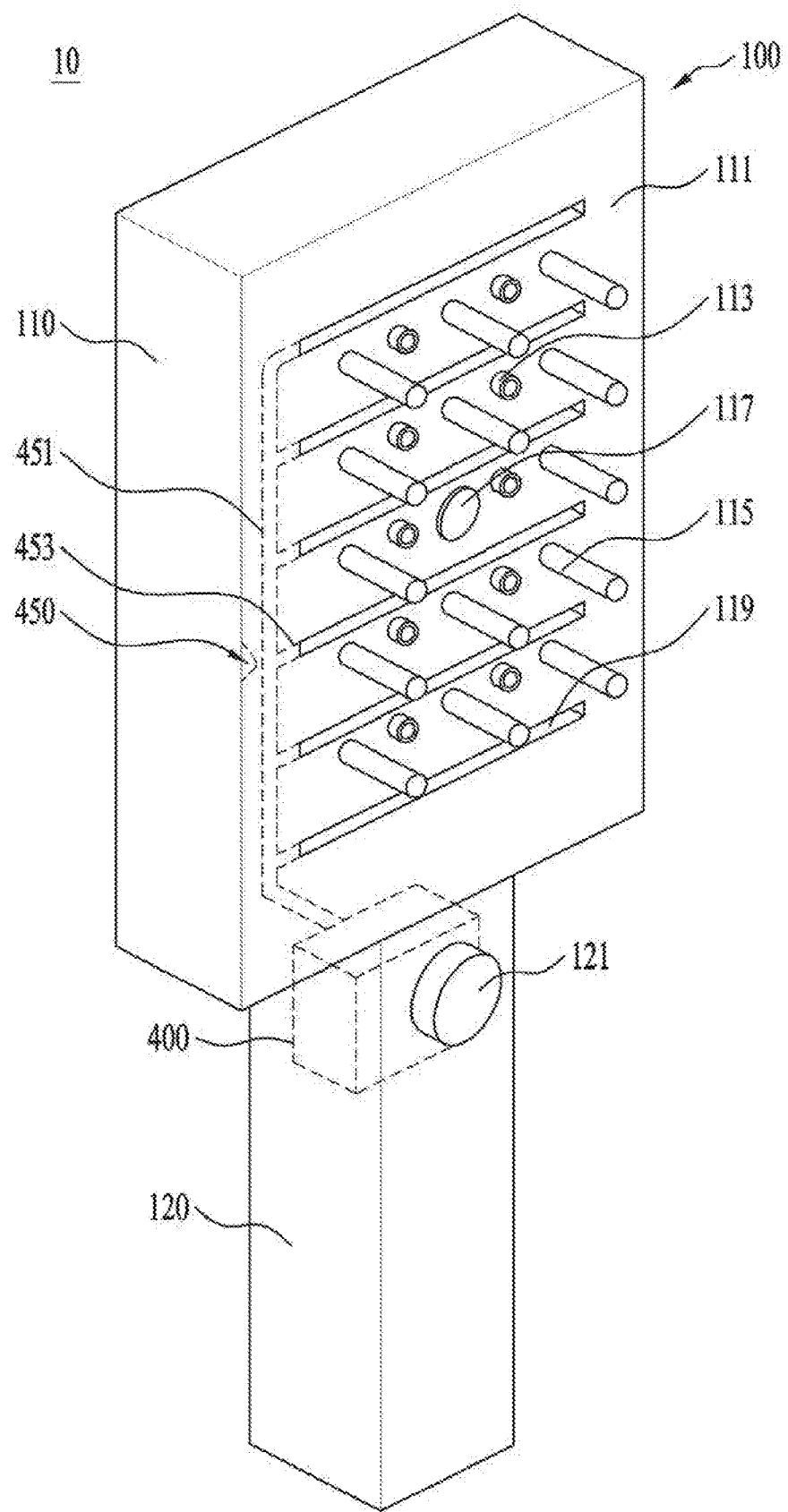
FIG. 6 is a perspective diagram illustrating a treatment device for a scalp in accordance with a second embodiment of the present disclosure.
Figure 7:
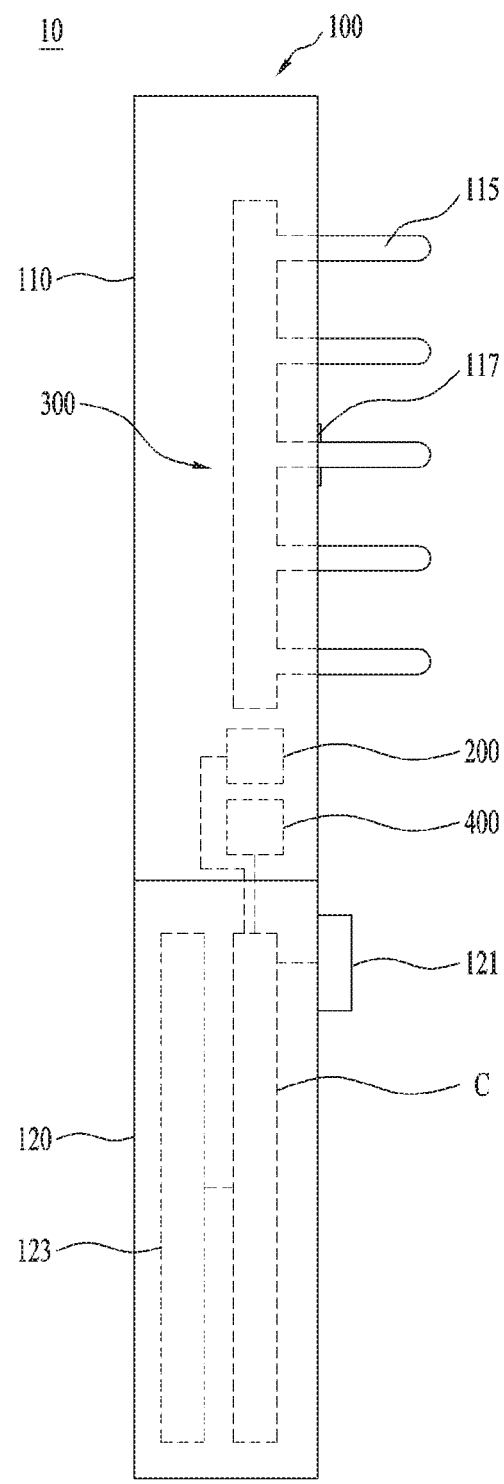
FIG. 7 is a side view of the treatment device for the scalp shown in FIG. 6.

FIG. 6 is a perspective diagram illustrating a treatment device for a scalp in accordance with a second embodiment of the present disclosure. FIG. 7 is a side view of the treatment device for the scalp shown in FIG. 6. Hereinafter, when describing the treatment device for the scalp in accordance with the second embodiment, description of different technical features from the first embodiment shown in FIGS. 1 and 2 will be described and the same features and configuration with the first embodiment will be omitted or minimized.

Referring to FIGS. 6 and 7, the treatment device for the scalp 10 in accordance with the second embodiment may include a body 100 in which a plurality of light irradiation holes 113 are formed, a light generation unit 200 provided in the body 100, and a beam splitter 300 configured to dividedly refractionate the light generated in the light generation unit 200 into a plurality of lights and guide the refractionated lights toward the plurality of the light irradiation holes 113, which is equal to the treatment device for the scalp in accordance with the first embodiment mentioned above.

Meanwhile, the treatment device for the scalp 10 may further include a wind generation unit 400 provided in the body 100. One or more outlet holes 119 may be formed in one surface 111 of the body 100.

The wind generation unit 400 may be formed in a pen or piston shape. The specific shape of the wind generation unit 400 for air suction and for the production of exhaust air is known and detailed description thereof will be omitted.

Although not shown in the drawings, an air inlet hole may be provided in the body 100 to allow external air sucked therethrough by the wind generation unit 400.

Once the wind generation unit 400 is put into operation, the wind generated in the wind generation unit 400 may be exhausted outside via the outlet holes 119 formed in the surface 111 of the body 100.

A plurality of outlet holes 119 may be provided at preset intervals. For example, the outlet holes 119 may be extended in a traverse direction of the body 100 and disposed a preset distance apart from each other in a longitudinal direction of the body 100. At this time, one or more light irradiation holes 113 may be arranged between each two neighboring outlet holes.

In case the scalp is hidden by hair during the treatment of the scalp which uses the light irradiation, the wind generated in the wind generation unit 400 may be operated long enough to allow the irradiated light to reach the scalp. That is, the wind exhausted by the wind generation unit 400 may prevent the light irradiated toward the scalp from be interfered by the hair.

The treatment device scalp 10 in accordance with the second embodiment may further include a guide path 450 formed to guide the wind generated in the wind generation unit 400 toward the plurality of the outlet holes 119.

More specifically, the guide path 450 may be provided in the first body 110 and the wind generation unit 410 mentioned above may be provided in the second body 120. The outlet hole of the wind generation unit 410 and an inlet of the guide path 450 are connected with each other to allow fluid to be in fluid communication.

The guide path 450 may include an extended path 451 for initially guiding the wind exhausted from the wind generation unit 410, and a plurality of branched paths 453 branched from the extended 451.

The extended path 451 may be extended along a direction in which the outlet holes 119 are arranged distant from each other. The plurality of the branched paths 453 may be branched from the extended path 451 to communicate with the outlet holes 119, respectively.

Accordingly, the wind generated in the wind generation unit 400 may be distributed to the outlet holes 119 and exhausted uniformly.

The treatment device for the scalp 10 in accordance with the second embodiment may include a light generation unit 200, a controller (C) for controlling the wind generation unit 400, and a distance sensor 117 provided in the surface 111 of the body 100.

The distance sensor 117 may be arranged on the same plane surface with the surface 111 of the body 100. When the distance sensor 117 senses that the distance between the surface 111 of the body 100 and the scalp is in a preset range of distances, the wind generation unit 400 may start to be driven. In other words, when the distance between the surface 111 of the body 100 and the scalp is within the preset range of distances, wind is generated in the wind generation unit 400 and exhausted via the outlet holes 119.

When the distance between the surface 111 of the body 100 is within the present range of the distances, light may be generated in the light generation unit 200. In other words, when the distance between the surface 111 of the body 100 and the scalp is within the present range, the light generated in the light generation unit 200 may be irradiated via the light irradiation holes 113 formed in the surface 111 of the body 100.

More specifically, when the distance between the surface 11 of the body 100 and the scalp is within the preset range of the distances, wind may be exhausted via the outlet holes 119 and light may be irradiated via the light irradiation holes 113 simultaneously.

The description of the preset range is provided when describing the first embodiment and will be omitted accordingly.

When the user puts the combteeth 115 of the treatment device for the scalp 100 in contact with the user's scalp in a state of inputting a power signal via the power button 121, the wind exhausted via the outlet holes 119 blows away the hair and the light irradiated via the light irradiation holes 113 can be directly irradiated to the scalp without the interference of the hair.

In accordance with the embodiments of the present disclosure, light may be irradiated in the wide range of the scalp, using the minimum number of the light sources. Also, when the distance between the light irradiation holes and the scalp is within the present range of the distances, light may be automatically irradiated and wind may be automatically exhausted via the outlet holes. Accordingly, use convenience may be enhanced.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A treatment device for a scalp, the treatment device comprising:
   a body defining an exterior of the treatment device, the body having a surface in which a plurality of light irradiation holes are formed;
   a light generator provided in the body;
   a beam splitter configured to dividedly refractionate light generated in the light generator into a plurality of lights, and to guide the plurality of lights toward the plurality of the light irradiation holes, a travel direction of the light generated in the light generator being different from a travel direction of the plurality of lights;
   a plurality of combteeth protruding from one surface of the body;
   a distance sensor provided in the one surface of the body, the distance sensor configured to detect a distance between the one surface of the body and the scalp; and
   a controller operably coupled with the light generator and the distance sensor and configured to control the light generator to automatically generate the light when the distance between the one surface of the body and the scalp is a first distance that the plurality of combteeth are in contact with the scalp,
   wherein:
      the plurality of light irradiation holes are separated from the plurality of combteeth,
      the plurality of light irradiation holes is disposed at positions between the plurality of combteeth, respectively, and
      the distance sensor is disposed at a center of the one surface of the body, and wherein the beam splitter comprises:
      a reflector comprising a plurality of reflective surfaces configured to reflect the light generated in the light generator;
      a first lens spaced a preset distance apart from the reflector and configured to widen an irradiation range of light reflected by the reflector; and
      a plurality of guides configured to guide the light having passed the first lens to the plurality of the light irradiation holes, respectively.

2. The treatment device of claim 1, wherein the beam splitter refractionates the travel path of the light into a plurality of travel paths by reflecting the light generated in the light generator.

3. The treatment device of claim 2, wherein the plurality of lights are guided to different ones of the light irradiation holes.

4. The treatment device of claim 1, wherein the first lens comprises a plurality of convex portions which are convex toward the plurality of the reflective surfaces.

5. The treatment device of claim 1, wherein the plurality of the reflective surfaces are provided in a lower surface of the reflector, and
   wherein the lower surface of the reflector is stepped and is inclined towards the first lens and away from the light generator.

6. The treatment device of claim 1, further comprising a plurality of guide lenses, each guide having a respective one of the guide lenses arranged in an end of the guide,
   wherein each guide lens is configured to widen an irradiation range of the lights guided by the guides.

7. The treatment device of claim 6, wherein the plurality of reflective surfaces are provided in an upper surface of the reflector, and
   wherein the upper surface of the reflector is stepped and is inclined towards the guide lenses and away from the light generator.

8. The treatment device of claim 1, wherein the light generator comprises:
   a light source; and
   a second lens arranged between the light source and the beam splitter, the second lens being configured to facilitate horizontal irradiation of the light toward the beam splitter.

9. The treatment device of claim 1, further comprising:
   a wind generator provided in the body,
   wherein wind generated in the wind generator is exhausted via one or more outlet holes formed in the one surface of the body.

10. The treatment device of claim 9, wherein the one or more outlet holes include a plurality of outlet holes arranged at preset intervals, and
    wherein one or more of the light irradiation holes are arranged between each two neighboring outlet holes of the plurality of outlet holes.

11. The treatment device of claim 9, further comprising a guide path configured to guide the wind generated in the wind generator toward the plurality of outlet holes.

12. The treatment device of claim 9, wherein the controller is further configured to control the wind generator, and
wherein when a distance between the surface of the body and the scalp is within a preset range of distances, the wind generated in the wind generator is automatically generated.

13. The treatment device of claim 12, wherein the comb-teeth extend within the preset range of the distances.

* * * * *